United States Patent
Cook et al.

(10) Patent No.: US 6,210,559 B1
(45) Date of Patent: Apr. 3, 2001

(54) USE OF $^{13}$C NMR SPECTROSCOPY TO PRODUCE OPTIMUM FISCHER-TROPSCH DIESEL FUELS AND BLEND STOCKS

(75) Inventors: Bruce R. Cook, Stewartsville; Paul J. Berlowitz, Glen Gardner; Bernard G. Silbernagel, Annandale; Debra A. Sysyn, Old Bridge, all of NJ (US)

(73) Assignee: Exxon Research and Engineering Company, Florham Park, NJ (US)

(*) Notice: Subject to any disclaimer, the term of this patent is extended or adjusted under 35 U.S.C. 154(b) by 0 days.

(21) Appl. No.: 09/373,697

(22) Filed: Aug. 13, 1999

(51) Int. Cl.[7] ............................. C10L 1/08; C07C 5/27
(52) U.S. Cl. ........................ 208/15; 585/14; 585/734; 208/27
(58) Field of Search ................. 585/14, 734; 208/15, 208/27

(56) References Cited

U.S. PATENT DOCUMENTS

| | | | |
|---|---|---|---|
| 5,378,348 | * | 1/1995 | Davis et al. ............................ 208/27 |
| 5,689,031 | * | 11/1997 | Berlowitz et al. .................... 585/437 |
| 5,807,413 | * | 9/1998 | Wittenbrink et al. ................. 208/15 |
| 5,814,109 | | 9/1998 | Cook et al. ............................ 44/300 |
| 5,895,506 | * | 4/1999 | Cook et al. ............................ 208/27 |

* cited by examiner

*Primary Examiner*—Jacqueline V. Howard
(74) *Attorney, Agent, or Firm*—Ronald D. Hantman (57) ABSTRACT

The present invention is a process for producing a distillate fuel heavier than gasoline. The process is a Fischer-Tropsch (hydrocarbon synthesis) process that includes using $^{13}$C NMR to measure cetane number and a cold flow property in order to optimize the process. Cold flow properties include cold filter plugging point, cloud point and pour point.

26 Claims, 6 Drawing Sheets

USE OF $^{13}$C NMR SPECTROSCOPY TO PRODUCE OPTIMUM FISCHER-TROPSCH DIESEL FUELS AND BLEND STOCKS

BACKGROUND OF THE PRESENT INVENTION

The present invention is a process for producing a distillate fuel heavier than gasoline. In particular, it is a process to optimize the production of a distillate from a hydrocarbon synthesis process. The use of Fischer-Tropsch (hydrocarbon synthesis) liquids as pure or as a component of distillate fuels is well known in the art. The products of the Fischer-Tropsch synthesis are predominantly normal paraffins. Economically it is desirable to operate Fischer-Tropsch catalysis at the highest possible Schulz-Flory alpha, in order to minimize undesirable light paraffins. High alpha operation over high activity cobalt catalysts, results in a high boiling, paraffinic wax product that is unsuitable for direct distillate blending. A high quality diesel blend stock is typically produced from the high Schulz-Flory product using hydroisomerization and or mild hydrocracking of the 700° F.$^+$wax. Sie, S. T. [Catalysis Letters 1990, 7, 253–270], invokes the hydroconversion of the entire hydrocarbon synthesis product. This hydroconversion results in 100% paraffinic products, although the degree of branching may vary. One of the great advantages of Fischer-Tropsch derived diesel fuels is their high inherent cetane number. There is a great incentive to maximize the cetane of the fuel in order to increase its value as a diesel blend stock, however, the product diesel must also meet any appropriate cold flow specifications, such as diesel cloud point or cold filter plugging point (CFPP). High cetane number corresponds with high molecular weight and low levels of branching, while cold flow often requires lower molecular weights and high levels of branching. Optimization of these two properties, either in blending or in actual plant operation is unwieldy due to the time consuming nature of both engine cetane and CFPP determinations. The present invention uses $^{13}$C NMR to rapidly determine both cetane and cold flow properties. These determinations are then used to optimize both product blending and unit operation. More detailed information about the molecular structure is also provided by the $^{13}$C NMR analysis and can serve as a valuable process diagnostic.

SUMMARY OF THE PRESENT INVENTION

The present invention is a process for producing a distillate fuel heavier than gasoline. The process uses Fischer-Tropsch (hydrocarbon synthesis) products from which the distillate fuel is produced. The process includes hydroisomerization selectivity and conversion which are typically controlled by catalyst selection, and variation of process conditions such as temperature, pressure, space velocity or gas treat rate. Any of these parameters could result in a wide range of diesel properties, such as cetane and cold flow properties. Therefore, in its broadest aspect, the present invention comprises obtaining the $^{13}$C NMR spectrum of the distillate product and determining numbers representative of the engine cetane number and a cold flow property in a process for producing a distillate fuel heavier than gasoline, wherein the distillate fuel is produced from a Fischer-Tropsch product that is hydroisomerized, blended and fractionated. In a preferred embodiment, cetane number and a cold flow property are determined by $^{13}$C NMR in order to optimize the distillate fuel production process. Cold flow properties include cold filter plugging point, cloud point, pour point and low temperature flow test. Cetane number and cold flow properties of all paraffinic diesel fuels are essentially inversely correlative properties. High cetane number corresponds with high molecular weight and low levels of branching, while cold flow often requires lower molecular weights and/or higher levels of branching. The position of the branches along the molecular backbone can also significantly influence both engine cetane and CFPP. Optimization of these two properties, either in blending or in actual plant operation is unwieldy due to the time consuming nature of both engine cetane and CFPP determinations. The present invention uses $^{13}$C NMR to rapidly determine both cetane and cold flow properties and the use of said determinations to optimize both product blending and unit operation.

A preferred embodiment of the present invention includes the steps of separating and selectively treating the product of a Fischer-Tropsch process. The initial separation is a heavier fraction (a) and a lighter fraction (b). The lighter fraction (b) is further separated using a temperature separator having an adjustable temperature into at least two fractions: (i) at least one fraction including light normal paraffins, and (ii) at least one fraction including heavy normal paraffins wherein the separation between light and heavy paraffin fractions is determined by the temperature. At least a portion of the heavier fractions (a) and at least a portion of the (b)(ii) fractions are then hydroisomerized and then blended with at least a portion of the fraction of (b)(i) to produce a blended stream. This blended stream is then distilled and the $^{13}$C NMR spectrum of the distillate product is obtained, determining numbers representative of the engine cetane number and a cold flow property. The cold flow property may be cold filter plugging point, cloud point or pour point. The temperature of the separator is adjusted in response to the $^{13}$C NMR data to optimize cetane number and the cold flow property.

DESCRIPTION OF THE PREFERRED EMBODIMENT

Figure 1:
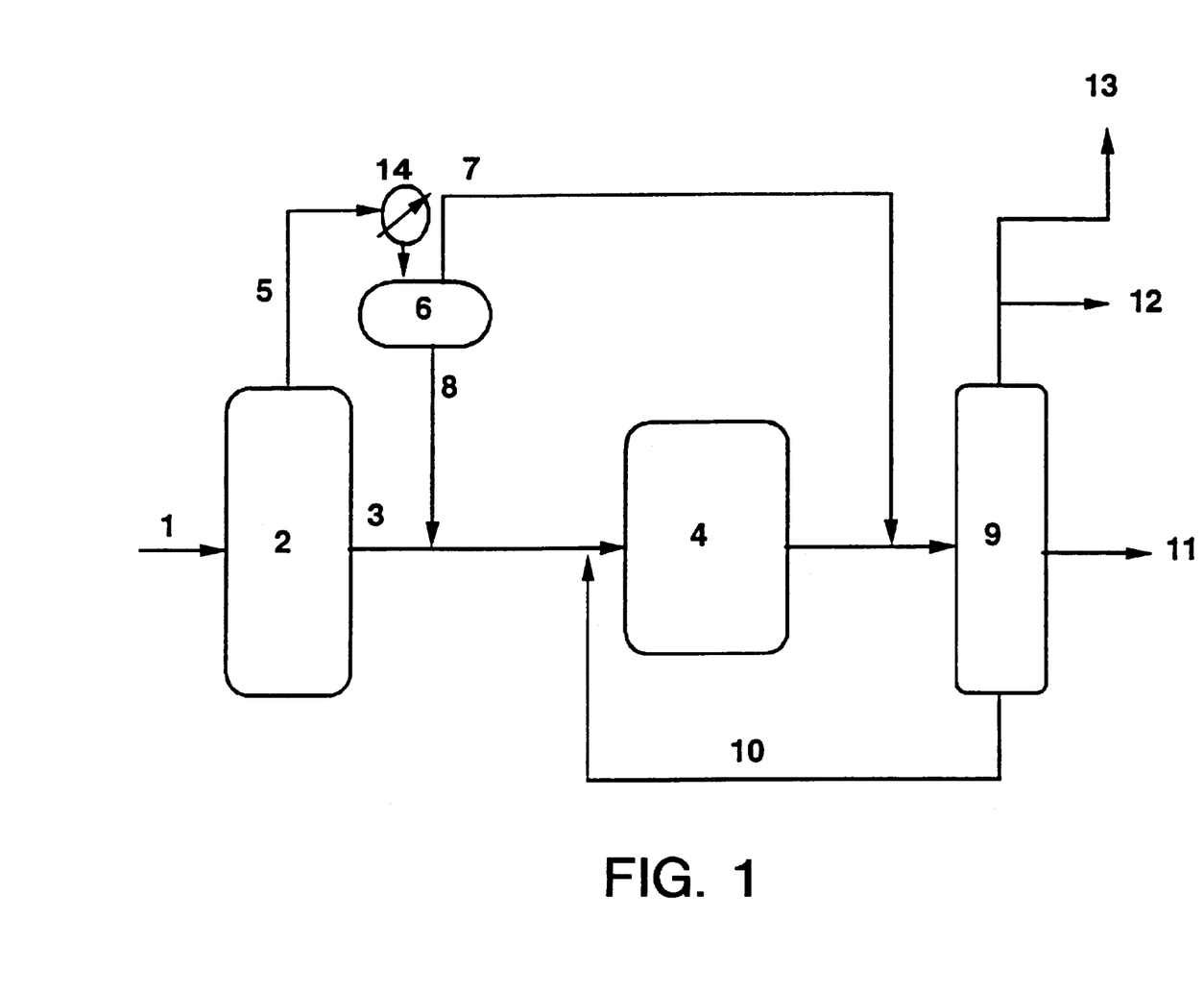
FIG. 1 shows a schematic diagram of an embodiment of the process of the present invention.

The present invention includes the use of $^{13}$C NMR to rapidly determine both cetane and cold flow properties and the use of these determinations to optimize both product blending and unit operation. A non-limiting example of such a unit optimization is as follows. A basic upgrading flow plan is shown in FIG. 1. In this plan, carbon monoxide and hydrogen synthesis gas (1) is sent to the Hydrocarbon Synthesis (HCS) unit (2). The HCS reactor configuration is not critical to this invention and could be any of the many HCS reactor configurations well known in the art. These include but are not limited to: slurry, fixed, and fluidized bed configurations. Catalyst formulation is also not critical to this invention and could include any of the HCS catalysts well known in the art, although cobalt based catalysts could be particularly preferred for this invention, because they tend to produce a heavier waxy product. The 700° F.⁺ product reactor wax (3) is sent to the hydroisomerization—(H/I) unit (4), where the 700° F.⁺wax undergoes H/I and mild hydrocracking—(H/C), such that 700° F.⁻distillate product is produced. Once again the reactor configuration for the H/I unit is not critical to this invention, and may be chosen from those well known in the art for heavy paraffin H/I and/or mild H/C. Typical configurations include but not limited to fixed and slurry bed operation. By means of this invention the conditions of the isomerization unit, including temperature and pressure are controlled using desired $^{13}$C NMR resonances as a guide.

The HCS overhead 700° F.⁻fraction (5) is flashed in separator (14) such as to form a lighter (7), and heavier (8) fraction. By means of this invention the flash point can be adjusted so that only the minimal amount of heavy paraffins are hydroisomerized in order to meet cold flow properties (CFPP, cloud point, etc.) using desired $^{13}$C NMR resonances as a guide. The heavier fraction (Stream 8) is then sent to HI(4) where the heavy paraffins are hydroisomerized to their corresponding iso paraffins. The lighter portion is usually sent directly to final distillation (9) where it is blended with the product of hydroisomerization and the final diesel fuel of the appropriate cutpoints is produced. The lighter portion could also be hydrotreated or hydroisomerized, if appropriate. The products from final distillation (9) include diesel fuel (11), naphtha (12), and C1–C4 gas (13).

$^{13}$C NMR Chemical Shifts

Carbon-13 NMR has a large range of chemical shifts (0–250 ppm), which offers an excellent opportunity for chemical shift characterization of different carbons. For a simple hydrocarbon system, the range for aliphatic carbons is ~0–50 ppm. Additivity rules can be used to determine estimated chemical shifts for a carbon in a given molecular structure. Extensive tables correlating chemical shifts with molecular structure have been established and useful handbooks of $^{13}$C NMR are available, see, e.g., E. Breitmaier, W. Voelter, "Carbon-13 NMR Spectroscopy", VCH, New York (1990).

NMR Software (such as that produced by Advanced Chemistry Development, Inc.) are useful in simulating NMR spectra for various molecules and relating structural trends in the chemical shift.

Several "rules of thumb" emerged from this chemical shift-structural analysis:

1. Methyl groups lie between ~5 and 22 ppm and methylenes lie between ~22 and 50 ppm. There is a small amount of overlap in the regions where methyl and methylene carbons can occur.
2. Methine and quaternary carbons fall between ~20 and 40 ppm with a significant amount of overlap with methylene carbons.
3. The signature observed for carbons at the end of a long chain normal paraffin is very characteristic: 14.2 - - - 22.9 - - - 32.2 - - - 29.6 - - - 29.9 - - -. Carbon atoms five or more sites from the end of a normal paraffin or four or more carbons from a branch will have a chemical shift near 29.9 ppm.
4. Branching of paraffins will introduce new shifts for the tertiary carbon sites and for those carbons 1–3 atoms from a branch. There are characteristic shifts for the methyls associated with short chain branches. Pendant methyls have methyl shifts in the vicinity of 19.1–19.7 ppm, the terminal methyls on pendant ethyls are at 10.8 ppm.
5. Tertiary sites for pendant methyls have a wide chemical shift range from 28–36 ppm. Tertiary sites for pendant ethyls range from 35–41 ppm. Tertiary sites for pendant propyls and butyls overlap significantly with pendant methyls.
6. New peaks will be introduced for multibranched molecules if the branches are close together. Vicinal methyls, methyls on adjacent carbons, have shifts from 15–19 ppm. Methylenes in the center of two methine carbons of methyl branches have shifts from 44–49 ppm.

While there is considerable chemical shift overlap between methylene, tertiary and quaternary sites, these different sites can be distinguished by proton-carbon polarization transfer (DEPT) NMR experiments.

The formalism for paraffin $^{13}$C NMR structure assignments used herein were obtained as discussed above and are summarized in FIG. 2. Five distinctive $^{13}$C resonances are observed for normal paraffins as well as for unsubstituted ends of isoparaffins. Carbon associated with the free end methyl termini, i.e., those ends that contain no branches, are referred to as $\alpha$ with a resonance at 14.0 ppm. In this study the actual number of free end methyls is calculated by subtracting the integrated peak intensity for p- and t-butyl (see below). This formalism avoids double counting ends. The free end methylenes one to three carbons from the methyl terminus are referred to as $\beta$, $\gamma$, and $\delta$, and have resonances at 22.8, 32.0, and 29.5 ppm, respectively. Carbon atoms adjacent to a branch point also have their chemical shifts perturbed and these absorptions are referred to as $\alpha'$, $\beta'$, and $\gamma'$ respectively, with shifts of 19.8, 37.4, and 27.4 ppm. Carbons over four carbons away from a terminus or three carbons away from a branch point are termed $\epsilon$, and exhibit resonances at or near 29.9 ppm.

Figure 2:
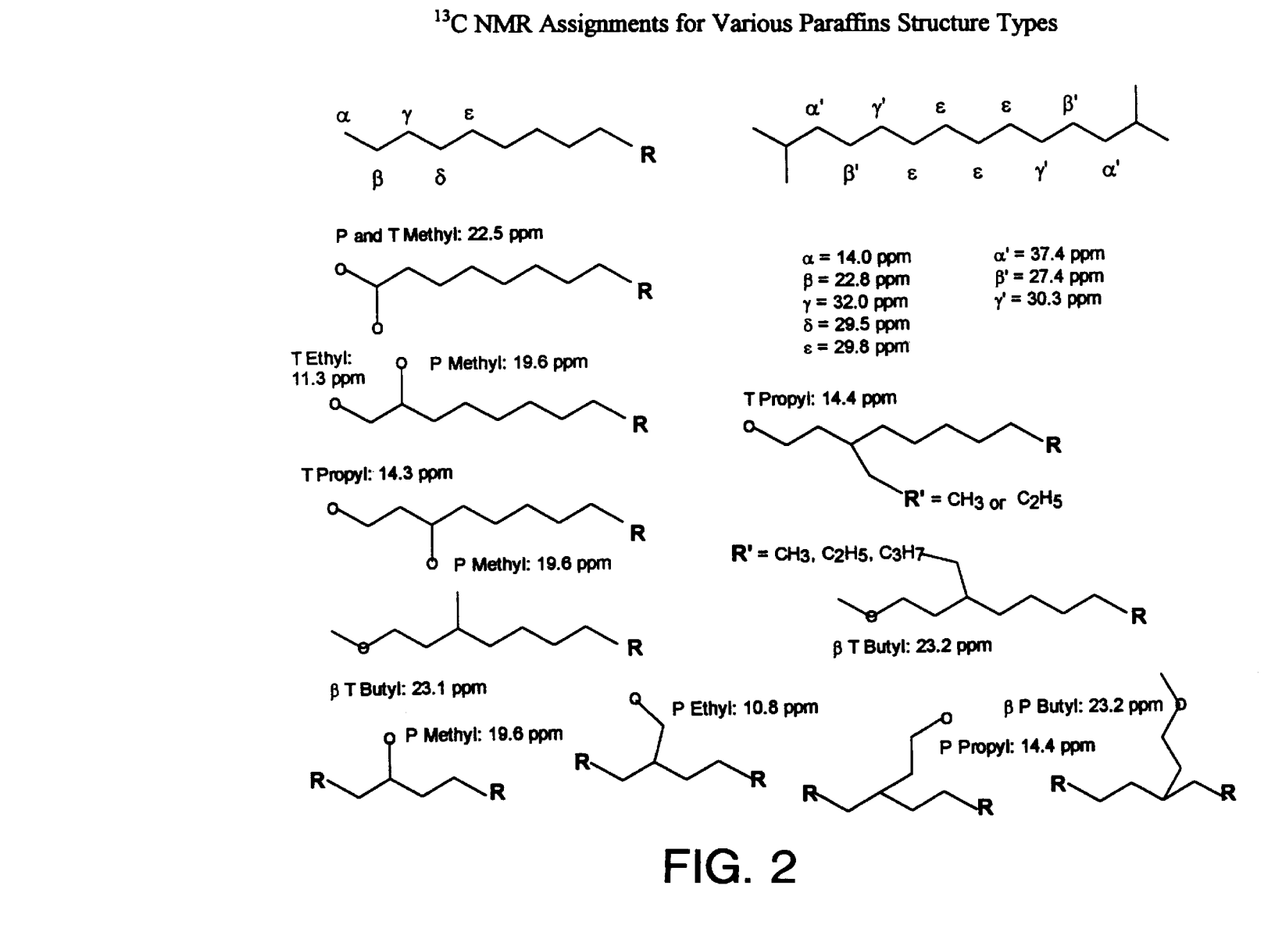
FIG. 2 shows the paraffin $^{13}$C NMR structure assignments used in the present invention.

In addition to the $\alpha$, $\beta$, $\gamma$, $\delta$, and $\epsilon$ for free ends, $^{13}$C NMR of isoparaffins show the distinctive resonances for the methyl carbon in methyl, ethyl, and propyl groups, and distinctive resonances for the $\beta$ methylene carbon for butyl groups. Two classes of methyl, ethyl, propyl, and butyl groups are observed. These are termed pendant (P) and terminal (T). Pendant groups are true substituents where the methyl (19.6 ppm), ethyl (10.8 ppm), propyl (14.4 ppm), and butyl (B) methylene resonance (23.2 ppm) are attached to a tertiary carbon attached to two alkyl groups with more carbons than the substituent. Terminal groups are not true substituents but are rather special resonances that are generated by methyl substitution near the end of the chain. Significant differences are observed for T vs. P methyl (22.5 vs. 19.6 ppm) and ethyl (11.3 vs. 10.8 ppm), whereas only slight differences are observed for T vs. P propyl (14.3 vs. 14.4 ppm) and butyl B methylene resonance (23.1 vs. 23.2 ppm). Ethyl or greater substitution shifts the T-propyl and butyl resonances to the same value as for the corresponding P groups. For dibranched species it is assumed that carbons three removed from the methyl branch will exhibit a $\gamma$ resonance and those more Man four away will exhibit a e resonance.

Experimental Examples

EXAMPLE 1

$^{13}$C NMR spectra were acquired for each F-T fuel used in this study at a frequency of 125.7 MHz in a Varian NMR Spectrometer for which the proton resonance frequency is 500 MHz. Experiments were done with and without $Cr^{3+}$ relaxation agents and nearly identical intensities were obtained for all components of the spectrum for both samples. Assignments of the individual peaks to specific carbon types were done on the basis of the chemical shifts, with the use of DEPT NMR sequences to discriminate methyl and methylene carbons in cases where the chemical shift assignments were ambiguous. The integrated intensities were recorded for peaks at the following chemical shifts.

| Structural Type | Chemical Shift in ppm |
|---|---|
| $\alpha^*$ | 14.0 |
| $\beta$ | 22.8 |
| $\chi$ | 32.0 |
| $\gamma$ | 29.5 |
| $\epsilon$ | 29.9 |
| T-Methyl | 22.5 |
| T-Ethyl | 11.3 |
| T-Propyl | 14.3 |
| T-Butyl | 23.1 |
| P-Methyl | 19.6 |
| P-Ethyl | 10.8 |
| P-Propyl | 14.4 |
| P-Butyl | 23.2 |
| Total Aliphatic Carbon | 0–50 |

The mole percent of each carbon type is calculated by dividing the integrated area of each carbon type by the total integration for total aliphatic carbon and multiplying by 100. In addition to the mole % carbon of each structure type, the following factors were mathematically determined.

The actual percent of $\alpha$ carbons is calculated as: $\alpha = \alpha^* - $ T-Butyl (23.1 residence)–P-Butyl (23.2 residence)

Average Carbon Number (C#)=(Mole % $\alpha$+T-Methyl+T-Ethyl+T-Propyl)/2

Free Carbon Index (FCI)=(Mole % $\epsilon$)*(Mole % $\alpha$+T-Methyl+T-Ethyl+T-Propyl)200

Free Carbon Index 2 (FCI2)=(Mole % $\epsilon$+Mole % $\delta$)*(Mole % $\alpha$+T-Methyl+T-Ethyl+T-Propyl)/200

Free Carbon Index 3 (FCI3)=(Mole % $\epsilon$+Mole % $\delta$+Mole % $\gamma$)*(Mole % $\alpha$+T-Methyl+T-Ethyl+T-Propyl)/200

Number of Side Chains (Ns)=
(Mole % P-Methyl+Mole % P-Ethyl+Mole % P-Propyl+Mole % P-Butyl)* (Mole % $\alpha$+T-Methyl+T-Ethyl+T-Propyl)/200

Normalized $\alpha$(N$\alpha$) Mole % $\alpha$*(Mole % $\alpha$+T-Methyl+T-Ethyl+T-Propyl)/2

Normalized $\beta$(N$\beta$)=Mole % $\beta$*(Mole % $\alpha$+T-Methyl+T-Ethyl+T-Propyl)/2

Normalized $\gamma$(N$\gamma$)=Mole % $\gamma$*(Mole % $\alpha$+T-Methyl+T-Ethyl+T-Propyl)/2

Normalized $\delta$(N$\delta$)=Mole % $\delta$*(Mole % $\alpha$+T-Methyl+T-Ethyl+T-Propyl)/2

Normalized $\epsilon$(N$\epsilon$)=Mole % $\epsilon$*(Mole % $\alpha$+T-Methyl+T-Ethyl+T-Propyl)/2

Normalized T-Methyl (NTMe)=Mole % T-Methyl*(Mole % $\alpha$+T-Methyl+T-Ethyl+T-Propyl)/2

Normalized T-Ethyl(NTEt)=Mole % T-Ethyl*(Mole % $\alpha$+T-Methyl+T-Ethyl+T-Propyl)/2

Normalized T-Propyl(NTPr) Mole % T-Propyl*(Mole % $\alpha$+T-Methyl+T-Ethyl+T-Propyl)/2

Normalized T-Butyl(NTBu) Mole % T-Butyl*(Mole % $\alpha$+T-Methyl+T-Ethyl+T-Propyl)/2

Normalized P-Methyl(NPMe)=Mole % P-Methyl*(Mole % $\alpha$+T-Methyl+T-Ethyl+T-Propyl)/2

Normalized P-Ethyl(NPEt)=Mole % P-Ethyl*(Mole % $\alpha$+T-Methyl+T-Ethyl+T-Propyl)/2

Normalized P-Propyl(NPPr)=Mole % P-Propyl*(Mole % $\alpha$+T-Methyl+T-Ethyl+T-Propyl)/2

Normalized P-Butyl(NPBu)=Mole % P-Butyl*(Mole % $\alpha$+T-Methyl+T-Ethyl+T-Propyl)/2

EXAMPLE 2

Figure 3:
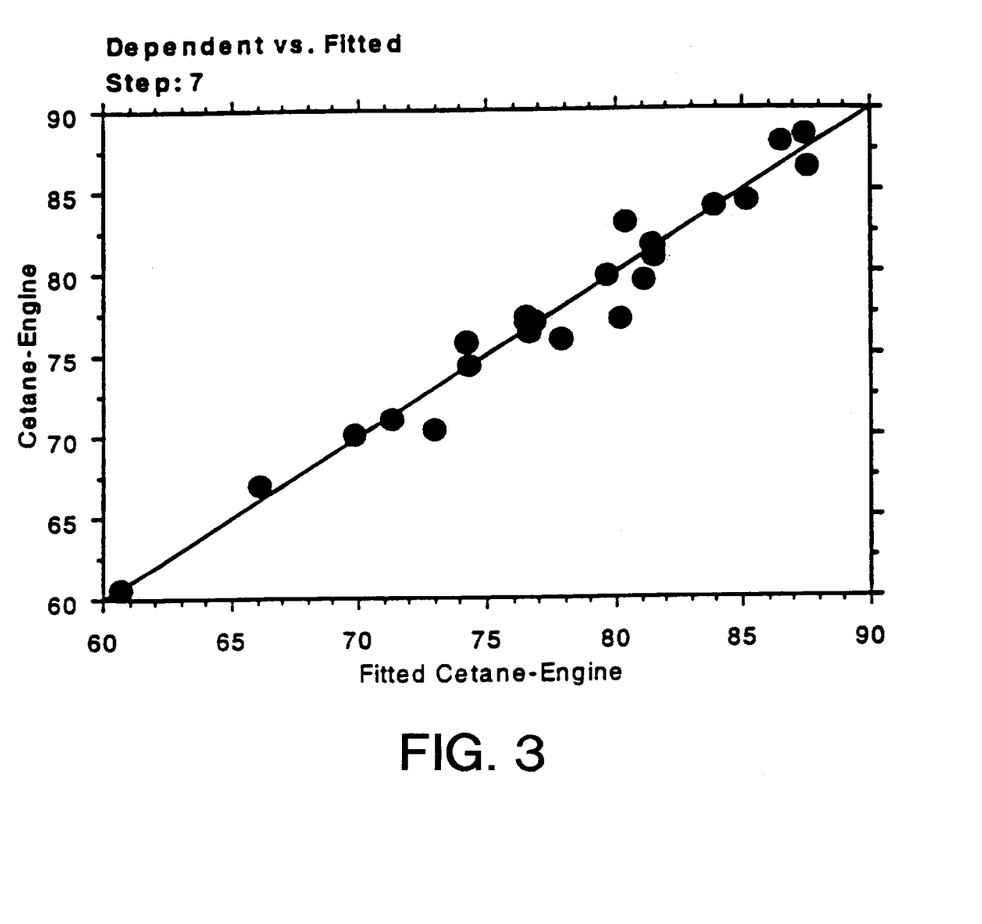
FIG. 3 shows the experimental vs. predicted engine cetane number using the formula in Example 2.

The engine cetane number of a series of 24 Fischer-Tropsch fuels were determined experimentally. The following formula can be used to determine the engine cetane number of a fuel from a $^{13}$C NMR spectrum. A plot of experimental vs. predicted cetane number for this formula is shown in FIG. 3 below. The root mean squared residual error for this prediction is 1.5 cetane numbers. This value is comparable to the experimental reproducibility of the test.

Engine Cetane Number=$42.78*N\alpha - 42.36*N\gamma - 8.14*N\delta - (3.83 \times 10^{-9})*e^{C\#} + 36.19*Ln(FCI3) - 4.02*(1/FCI) - 14.46*Ln(Ns)$

EXAMPLE 3

Figure 4:
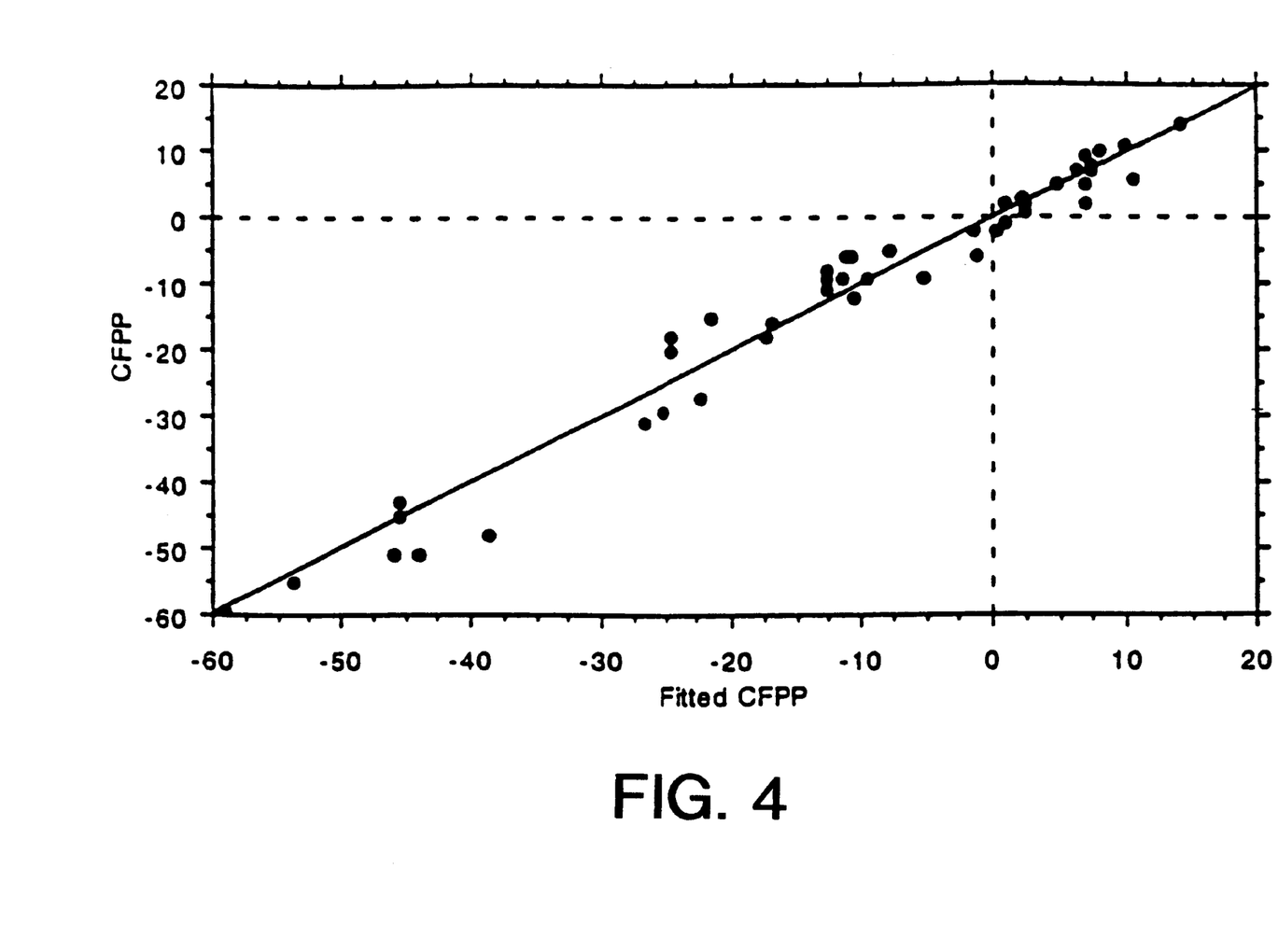
FIG. 4 shows the experimental vs. predicted cold filter plugging point using the formula in Example 3.

The cold filter plugging point (CFPP) of a series of 47 Fischer-Tropsch fuels were determined experimentally. The following formula can be used to determine the engine cetane number of a fuel from a $^{13}$C NMR spectrum. A plot of experimental vs. predicted cetane number for this formula is shown in FIG. 4. The root mean squared residual error for this prediction is 3.8 degrees. This value is comparable to the experimental reproducibility of the test.

CFPP=$-237.19 - 134.67*NTBu + 59.26*Ln(C\#) + (4.04 \times 10^{-10})*e^{C\#} + 40.33*Ln(FCI12) - (1.59 \times 10^{-4}*e^{FC13})$

EXAMPLE 4

Figure 5:
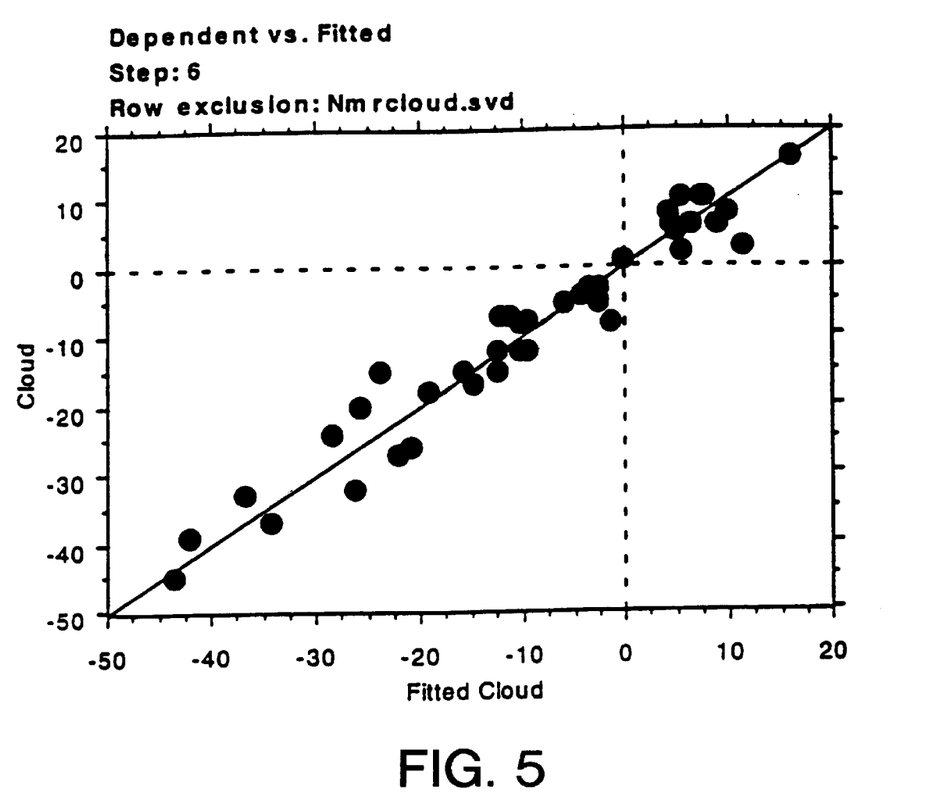
FIG. 5 shows the experimental vs. predicted cloud point using the formula in Example 4.

The cloud point of a series of 44 Fischer-Tropsch fuels were determined experimentally. The following formula can be used to determine the engine cetane number of a fuel from a $^{13}$C NMR spectrum. A plot of experimental vs. predicted cetane number for this formula is shown in FIG. 5. The root mean squared residual error for this prediction is 3.8 degrees. This value is comparable to the experimental reproducibility of the test.

Cloud Point=$-135.39 + 72.67*Ln(FCI) + 79.78/(FCI)$

EXAMPLE 5

Figure 6:
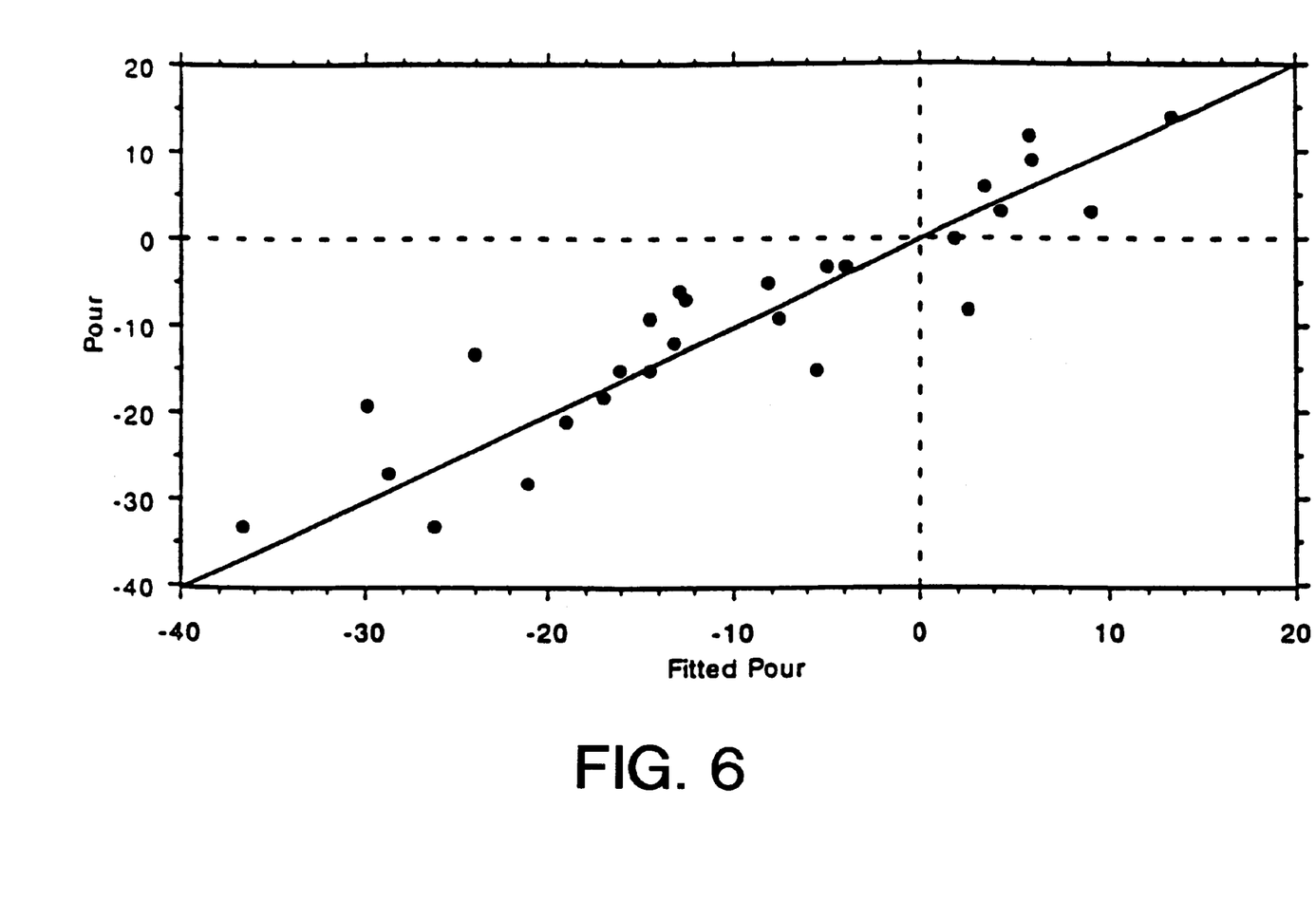
FIG. 6 shows the experimental vs. predicted pour point using the formula in Example 5.

The pour point of a series of 34 Fischer-Tropsch fuels were determined experimentally. The following formula can be used to determine the engine cetane number of a fuel from a $^{13}$C NMR spectrum. A plot of experimental vs. predicted cetane number for this formula is shown in FIG. 6. The root mean squared residual error for this prediction is 6.1 degrees. This value is comparable to the experimental reproducibility of the test.

Pour Point=$-16.67 + 9.38*N\epsilon - 221.25/FCI3$

What is claimed is:

1. In a process for producing a distillate fuel heavier than gasoline, wherein said distillate fuel is produced from a Fischer-Tropsch product that is hydroisomerized, blended and fractionated, the improvement which comprises optimizing said process by obtaining the $^{13}$C NMR spectrum of the distillate product and determining numbers representative of a physical or chemical property.

2. The process of claim 1 wherein said property is engine cetane number.

3. The process of claim 1 wherein said property is cold flow.

4. The process of claim 3 wherein said cold flow property includes cold filter plugging point, cloud point, and pour point.

5. The process of claim 3 wherein said cold flow property is cold filter plugging point.

6. The process of claim 3 wherein said cold flow property is cloud point.

7. The process of claim 3 wherein said cold flow property is pour point.

8. The process of claim 2 wherein said cetane number is determined by Engine Cetane Number=$42.78*N\alpha-42.36*N\gamma-8.14*N\delta-(3.83\times10^{-9})*e^{C\#}+36.19*Ln(FCI3)-4.02*(1/FCI)-14.46*In(Ns)$.

9. The process of claim 5 wherein said cold filter plugging point is determined by CFPP=$-237.19-134.67*NTBu+59.26*Ln(C\#)+(4.04\times10^{-10})*e^{C\#}+40.33*Ln(FCI2)-(1.59\times10^{-4})*e^{FCI3}$.

10. The process of claim 8 wherein said cold filter plugging point is determined by CFPP=$-237.19-134.67*NTBu+59.26*Ln(C\#)+(4.04\times10^{-10})*e^{C\#}+40.33*Ln(FCI2)-(1.59\times10^{-4})*e^{FCI3}$.

11. The process of claim 6 wherein said cloud point is determined by cloud point=$-135.39+72.67*Ln(FCI)+79.78/(FCI)$.

12. The process of claim 8 wherein said cloud point is determined by cloud point=$-135.39+72.67*Ln(FCI)+79.78/(FCI)$.

13. The process of claim 7 wherein said pour point is determined from pour point=$-16.67+9.38*N\epsilon-221.25/FCI3$.

14. The process of claim 8 herein said pour point is determined from pour point=$-16.67+9.38*N\epsilon-221.25/FCI3$.

15. A process for controlling a process for producing a distillate fuel heavier than gasoline comprising:
 (a) separating the product of a Fischer-Tropsch process into a heavier fraction and a lighter fraction;
 (b) further separating the lighter fractions using a temperature separator having an adjustable temperature into at least two fractions, (i) at least one fraction including light normal paraffins, and (ii) at least one fraction including heavy normal paraffins wherein the separation between light and heavy paraffin fractions is determined by the temperature;
 (c) hydroisomerizing at least a portion of the heavier fractions (a) and at least a portion of the (b)(ii) fractions at hydroisomerization conditions and recovering the hydroisomerization product;
 (d) blending at least a portion of the fraction of (b)(i) with at least a portion of the hydroisomerization product to produce a blended stream;
 (e) fractionating said blended stream and recovering a distillate product;
 (f) obtaining the $^{13}C$ NMR spectrum of the distillate product;
 (g) determining numbers representative of the engine cetane number and a cold flow property; and
 (h) adjusting said temperature of said separator in response to said numbers to optimize said engine cetane number and said cold flow property.

16. The process of claim 15 wherein said cold flow property includes cold filter plugging point, cloud point, and pour point.

17. The process of claim 16 wherein said cold flow property is cold filter plugging point.

18. The process of claim 16 wherein said cold flow property is cloud point.

19. The process of claim 15 wherein said cetane number is determined by Engine Cetane Number=$42.78*N\alpha-42.36*N\gamma-8.14*N\delta-(3.83\times10^{-9})*e^{C\#}+36.19*In(FCI3)-4.02*(1/FCI)-14.46*In(Ns)$.

20. The process of claim 16 wherein said cold flow property is pour point.

21. The process of claim 17 wherein said cold filter plugging point is determined by CFPP=$-237.19-134.67*NTBu+59.26*In(C\#)+(4.04\times10^{-10})*e^{C\#}+40.33*In(FCI2)-(1.59\times10^{-4})*e^{FCI3}$.

22. The process of claim 20 wherein said cold filter plugging point is determined by CFPP=$-237.19-134.67*NTBu+59.26*In(C\#)+(4.04\times10^{-10})*e^{C\#}+40.33*In(FCI2)-(1.59\times10^{-4})*e^{FCI3}$.

23. The process of claim 18 wherein said cloud point is determined by cloud point=$-135.39+72.67*In(FCI)+79.78/(FCI)$.

24. The process of claim 20 wherein said cloud point is determined by cloud point=$-135.39+72.67*In(FCI)+79.78/(FCI)$.

25. The process of claim 19 wherein said pour point is determined from pour point=$-16.67+9.38*N\epsilon-221.25/FCI3$.

26. The process of claim 20 herein said pour point is determined from pour point=$-16.67+9.38*N\epsilon-221.25/FCI3$.

\* \* \* \* \*